United States Patent [19]

Kurokawa et al.

[11] Patent Number: 5,108,394
[45] Date of Patent: Apr. 28, 1992

[54] BONE FIXING DEVICE

[75] Inventors: Takahide Kurokawa; Takashi Matsushita; Isao Ohnishi, all of Tokyo; Shigemitsu Ogawa, Nagano; Tsuneo Yokotsuka, Nagano; Akio Nakazawa, Nagano, all of Japan

[73] Assignee: Kabushiki Kaisha Nagano Keiki Seisakusho, Japan

[21] Appl. No.: 578,564

[22] Filed: Sep. 6, 1990

[30] Foreign Application Priority Data

Sep. 8, 1989 [JP] Japan .................. 1-233279
Sep. 8, 1989 [JP] Japan .................. 1-233280

[51] Int. Cl.$^5$ .................................. A61B 17/56
[52] U.S. Cl. .................................. 606/59
[58] Field of Search .................. 606/53-59, 606/105

[56] References Cited

U.S. PATENT DOCUMENTS

| | | | |
|---|---|---|---|
| 2,250,417 | 7/1941 | Ettinger | 606/59 |
| 2,251,209 | 7/1941 | Stader | 606/59 |
| 2,333,033 | 10/1943 | Mraz | 606/59 |
| 2,346,346 | 4/1944 | Anderson | 606/59 |
| 4,628,922 | 12/1986 | Dewar | 606/59 |
| 4,978,348 | 12/1990 | Ilizarov | 606/59 |

FOREIGN PATENT DOCUMENTS 0024256  2/1981  European Pat. Off. .
2616059 12/1988  France .

Primary Examiner—Robert A. Hafer
Assistant Examiner—Michael Brown
Attorney, Agent, or Firm—Ladas & Parry

[57] ABSTRACT

A bone fixing device is disclosed in which a single rod member is arranged in a longitudinal direction of a bone, and at least two block members are mounted on the rod member so that the block members may be fixed to any desired positions in the axial direction and around the axis of the rod member. Pin holding mechanisms for holding a plurality of pins to be inserted into the bone are mounted on the block members, respectively. By the pin holding mechanisms, the pins are positionally adjustable around axes in the first and second directions which are preferably perpendicular to the axial direction. Also, an actuator is fixed to the rod member. One of the block members slidable relative to the rod member is moved in the axial direction relative to the rod member to thereby impart elongation/contraction force to the bone. A detector is fixed to the other member and is brought into contact with a contact located at an end of the rod member to thereby detect the repulsive force from the bone.

14 Claims, 9 Drawing Sheets

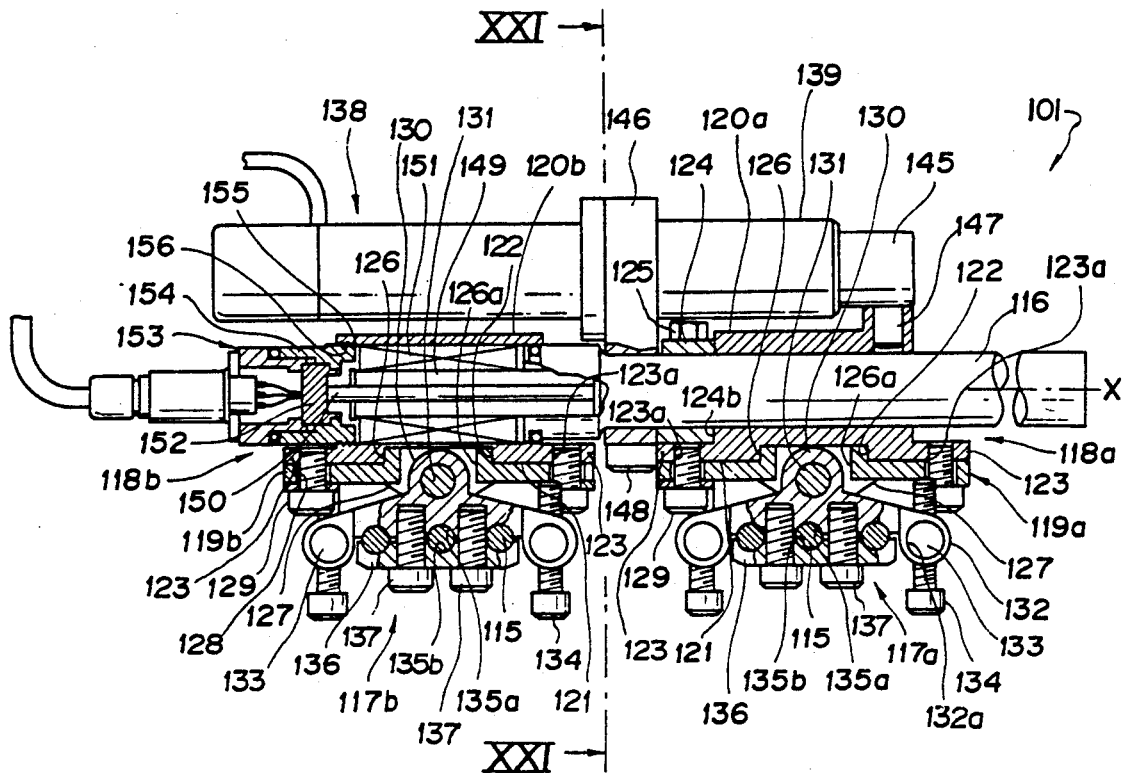
FIG. 19
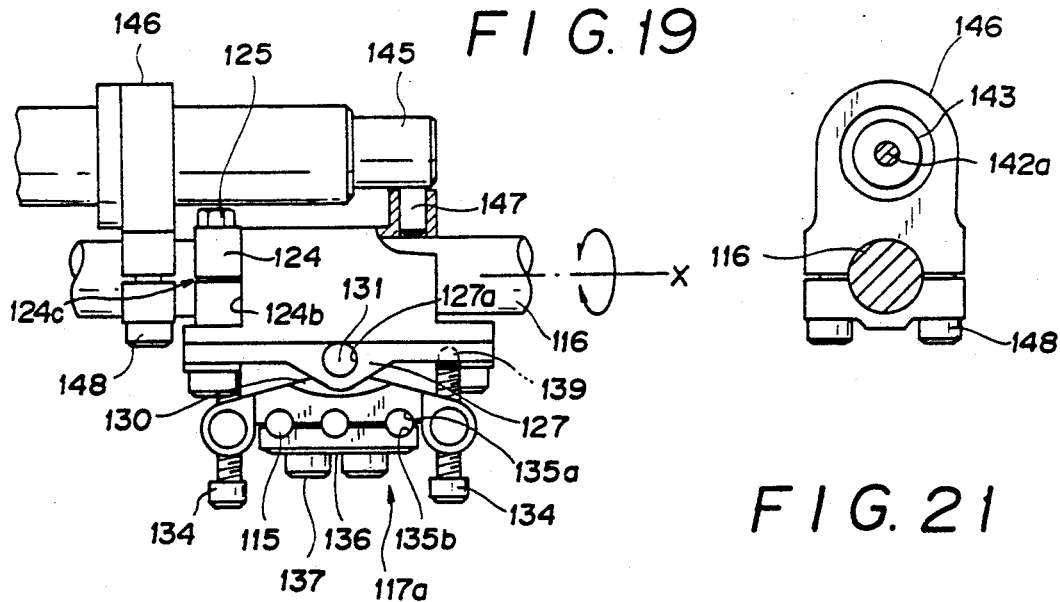
FIG. 20
FIG. 21

BONE FIXING DEVICE

BACKGROUND OF THE INVENTION

The present invention relates to a bone fixing device used as a plastic surgery or orthopedic instrument for fixing a broken portion of a bone and extending or contracting a bone.

In general, in case of a medical treatment, a bone fixing device is used as an orthopedic instrument for fixing the broken portion of the bone. The bone fixing device is used not only for simply fixing the bone but also controlling the extension/retraction of the bone. In addition, the bone fixing device is used for adjusting the extension/retraction of the bone.

The present inventors et al. of Japanese Patent application No. 63-139245 filed on Jun. 8, 1988 relating to a bone fixing device having a fixture function. The fixing device is composed of the following components: a body frame having a linear rigidity and extending in an X-direction along the longitudinal direction of the bone; two holding frames positionally adjustably attached to the body frame for holding insert pins extending in a Z-direction perpendicular to the X-direction to be inserted into the bone; swing plates extending in a Y-direction perpendicular to the X-and Y-directions and swingable about the axis of Z-direction; pin heads mounted on the swing plates and swingable about the axis of Y-direction for detachably holding the insert pins; and a position adjusting mechanism for shifting at least one of the two holding frames on the body frame.

However, in the bone fixing device, in order to rotate the block-like swing plates about the Z-axis, it is necessary to juxtapose a plurality of rod-like members and to clamp the swing plates between the rod-like members. Also, in order to rotate the pin heads about the Y-axis, it is necessary to splice the pin heads with the tip ends of the swing plates by using shaft members.

Accordingly, the bone fixing device suffers from such problems that the physical size is increased and its weight is increased. As a result, a large amount of loads should be paid for treating the device.

On the other hand, there has been proposed a bone fixing device which is capable of extending/retracting the bone as shown in Japanese Patent application No. 63-333943 filed on Dec. 30, 1988 by the present inventors et al. This device is provided with two pairs of pin holding members for holding pins to be inserted into the broken bone. Also, this device is provided with a rod-like member composed, in combination, of a solid rod and a sleeve into which the solid rod is retractably or extendably inserted. Each of the pin holding members is fixed to the solid rod and the sleeve, respectively. Furthermore, a casing of an actuator is fixed to the sleeve, whereas a screw rod which is used as a reciprocation part of the actuator is connected to the solid rod.

With such an arrangement, when a motor of the actuator is operated, its rotational torque is transmitted in order through a reduction gear means, a bevel gear, a worm, and a worm wheel to a screw sleeve, and the screw rod is extended or retracted relative to the screw sleeve in a telescopic manner to thereby shift the pin holding member to adjust the extention/retraction of the fixed bone.

Such adjustment of extension/retraction of the bone is carried out by detecting a strain caused by the screw rod end abutting against a load cell provided at one end of the screw sleeve.

However, if the force applied to the bone would be detected by the relative movement between the screw rod and the screw sleeve as described above, there would be a fear that the value detected by the load cell would be not correct due to the factors such as a generation of a strain of the screw rod.

Also, since the rod member is of the inner and outer double type, there would be a fear that there is a positional offset between the pin holding members when the rod member is telescopically moved.

SUMMARY OF THE INVENTION

Accordingly, an object of the invention is to provide a bone fixing device which is simplified in structure and light in weight, which may readily be handled in a medical treatment.

This and other objects of the invention are attained by providing a bone fixing device comprising:
a single rod member adapted to be disposed in a longitudinal direction of a bone;
at least two block members mounted on the rod member and fixable to any position in an axial direction and any angular position around the axial direction; and
pin holding means mounted on the respective block members for holding and positionally adjusting pins to be fixed to the bone around a first direction and a second direction which are different from the axial direction.

Also, another object of the invention is to provide a bone fixing device which is capable of detecting elongation/contraction force applied to the bone by using a detector with high precision.

According to another aspect of the invention, this and other objects are attained by providing a bone fixing device further comprising;
an actuator fixed to the rod member for moving in the axial direction one of the block members slidable relative to said rod member, thereby imparting elongation/contraction force to the bone;
a detector fixed to the other of said block members and coming into contact with a contact located at an end portion of the rod member for detecting a repulsive force from the bone; and
a control unit for receiving detection signals from the detector and for outputting command signals to the actuator.

BRIEF DESCRIPTION OF THE DRAWINGS

In the accompanying drawings;

FIG. 1 is a perspective view showing the bone fixing device;

FIG. 2 is a partially fragmentary plan view showing the device shown in FIG. 1;

FIG. 3 is a frontal view showing the device shown in FIG. 1;

FIGS. 4 to 6 show a block member shown in FIG. 1, in which FIG. 4 is a left side elevational view showing the block, FIG. 5 is a cross-sectional view taken along the line V—V of FIG. 6, FIG. 6 is a frontal view showing the block;

FIGS. 7 to 9 show a seat member shown in FIG. 1, in which FIG. 7 is a cross-sectional view taken along the line VII—VII of FIG. 9, FIG. 8 is a partially enlarged cross-sectional view showing the ball member of the device shown in FIG. 7, and FIG. 9 is a frontal view showing the seat member shown in FIG. 1;

FIGS. 10 to 12 show a pin holding member of the device shown in FIG. 1, in which FIG. 10 is a rear view, FIG. 11 is a plan view and FIG. 12 is a frontal view;

FIGS. 13 to 15 show a circular column to be inserted into an adjustment screw insert portion of the pin holding member, in which FIG. 13 is a perspective view, FIG. 14 is a frontal view and FIG. 15 is a cross-sectional view taken along line XV—XV of FIG. 14;

FIGS. 16 and 17 show a fastening member of the block member shown in FIG. 1, in which FIG. 16 is a frontal view and FIG. 17 is a side elevational view;

FIGS. 18 to 25 show a bone fixing device in accordance with a second embodiment of the invention, in which FIG. 18 is an overall schematic view showing the bone fixing device, FIG. 19 is a partially fragmentary plan view showing the device, FIG. 20 is a fragmentary plan view showing a primary part of a mounting portion of an actuator shown in FIG. 18, FIG. 21 is a cross-sectional view taken along the line XXI—XXI of FIG. 19, showing a fastening member of the actuator, FIG. 22 is a fragmentary plan view showing a reciprocating portion of the actuator, FIG. 23 is a schematic perspective view showing a positional relationship between the bone and the fixing device, FIG. 24 is an illustration of the fixing device including a control unit, and FIG. 25 is a graph showing a relationship between the medical treatment time and the reduction force applied from the bone;

DESCRIPTION OF THE PREFERRED EMBODIMENTS

A first embodiment of the present invention will now be described with reference to FIGS. 1 through 17.

Figure 1:
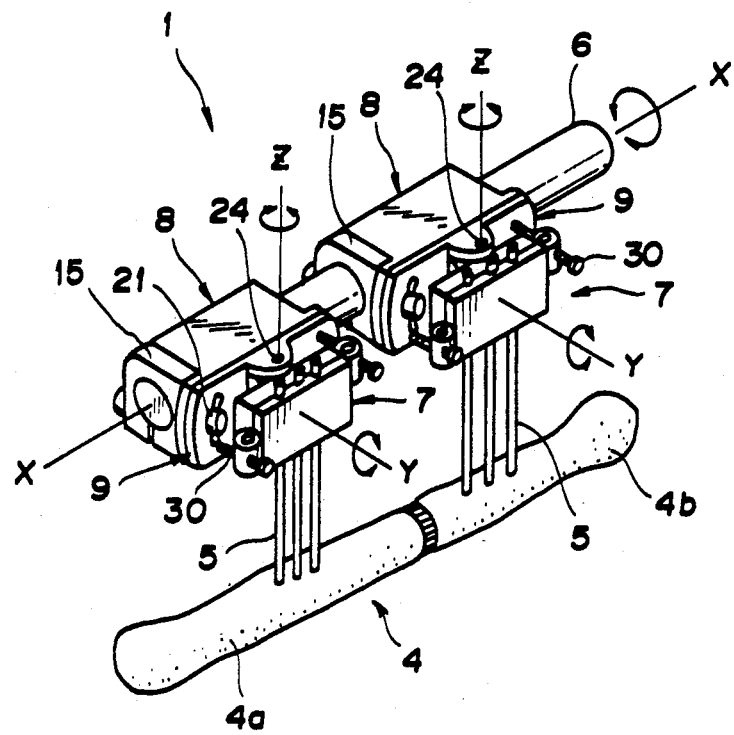
FIGS. 1 to 17 show a bone fixing device according to a first embodiment of the invention.

In FIG. 1, reference numeral 4 indicates a bone broken into two bone segments 4a and 4b. A bone fixing device 1 to which the invention pertains is attached to the broken bone 4. The attachment is performed by fixedly inserting pins 5 into the bone segments 4a and 4b, respectively.

Figure 2:
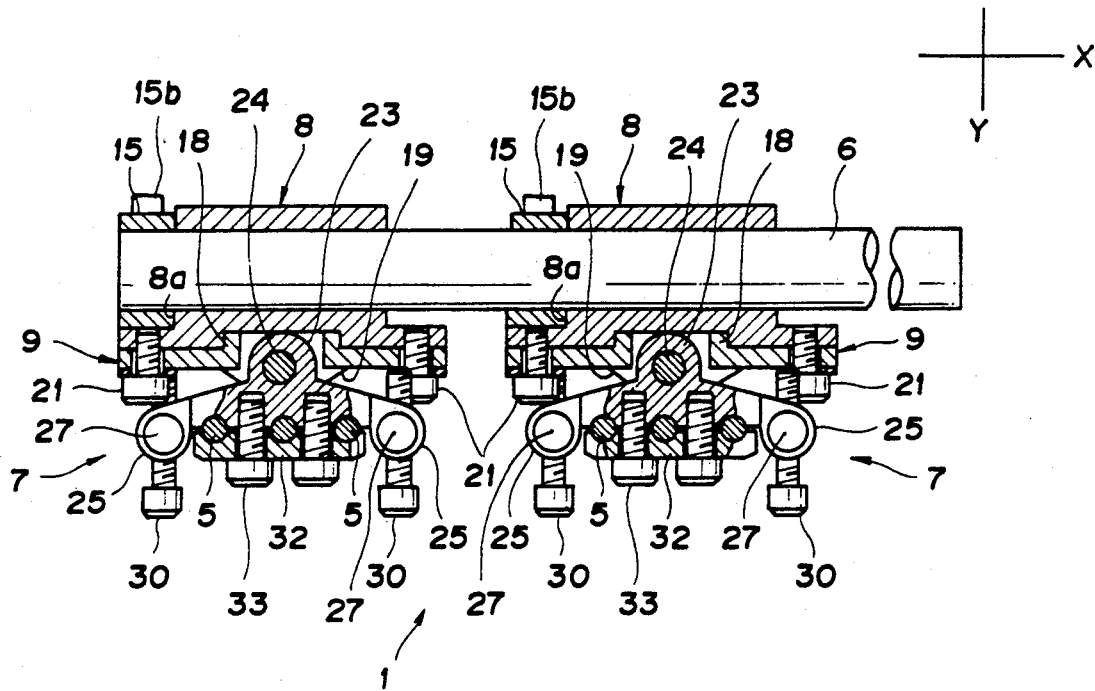
Figure 3:
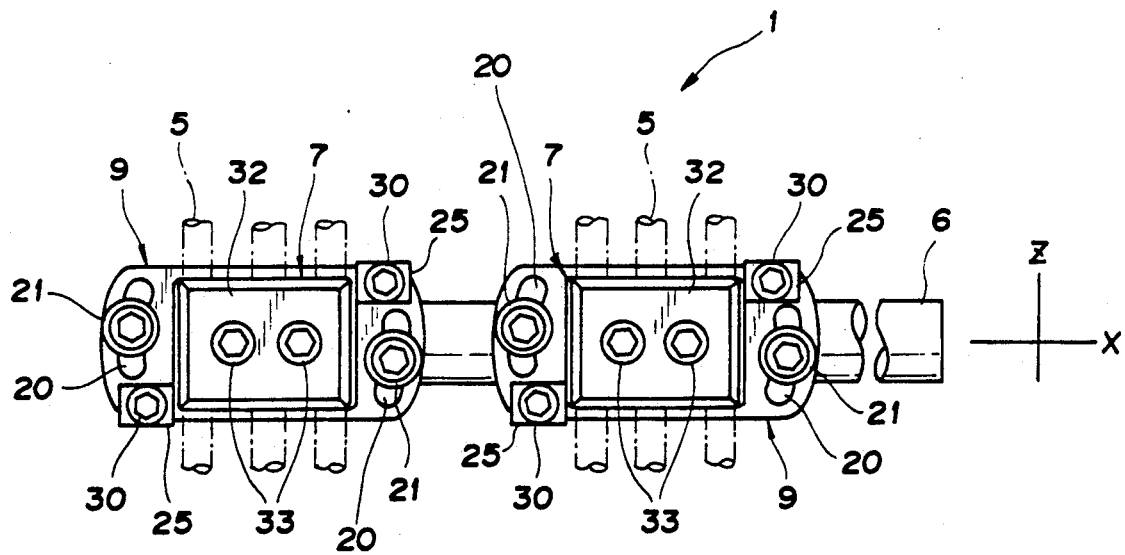

As shown in FIGS. 1 through 3, the bone fixing device 1 is provided with a single rod member 6 to be arranged along the longitudinal direction of the bone 4. Two pairs of pin holding members 7 for holding the pins 5 in the vertical direction are attached to the rod member 6. The axial direction of the rod member 6 is indicated by X. Each pin holding member 7 is mounted on the rod member 6 through an associated block member 8 and an associated seat member 9.

Figure 5:
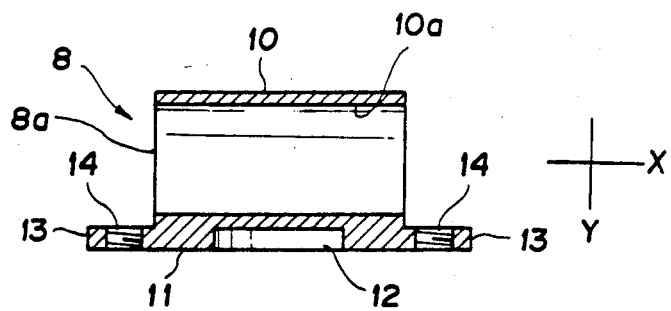
Figure 4:
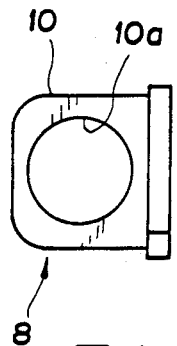
Figure 6:
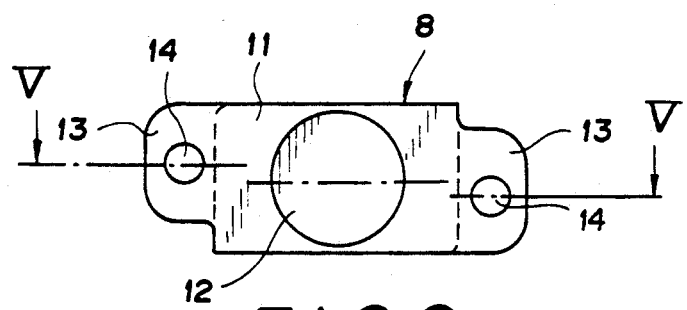
Figure 16:
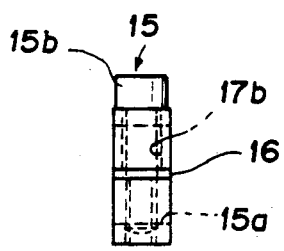
Figure 17:
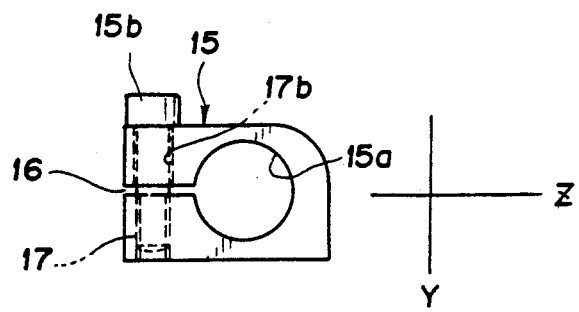
Figure 18:
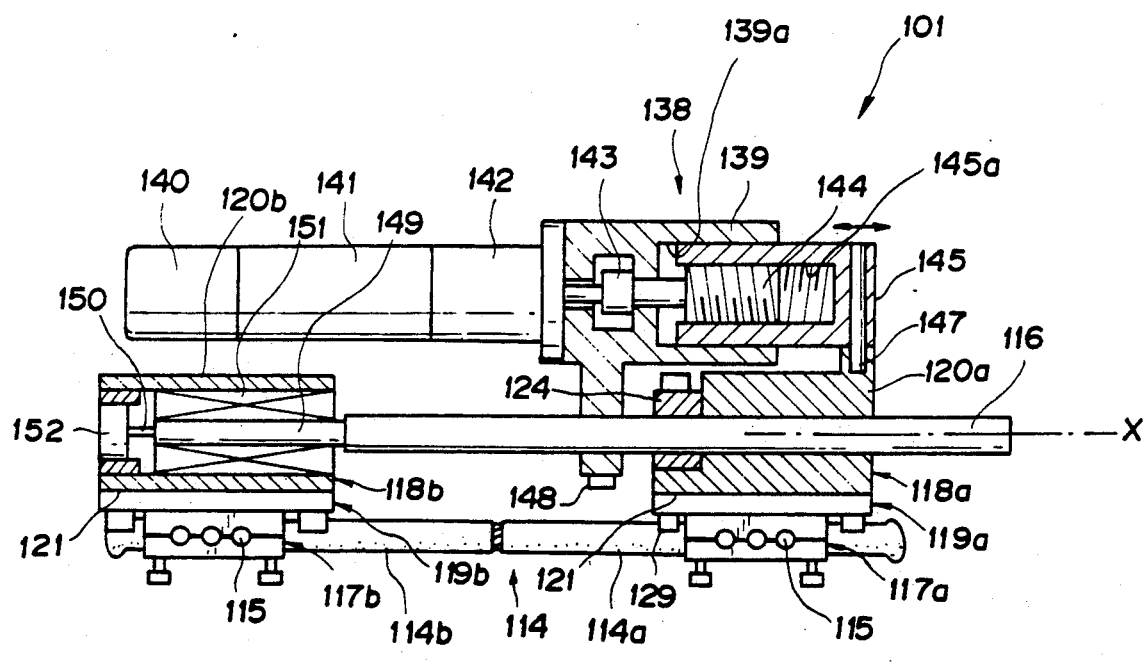

As best shown in FIGS. 4 to 6, each block member 8 is provided with a sleeve portion 10 having a hole 10a into which the rod member 6 is inserted. A flat surface 11 is formed in a parallel direction (X-direction) with the centeraxis of the sleeve portion 10. A circular recess 12 for bearing is formed in the central portion of the flat surface 11. A pair of flange portions 13 which are flush with the flat surface 11 are formed at both sides of the sleeve portion 10 (FIG. 5). Screw holes 14 are formed in the respective flange portions 13. As shown in FIGS. 16 and 17, fixing members 15 (FIG. 2) for fixing the block members 8 in desired position on the X-axis along the centeraxis of the rod member 6 are provided on the left side of an L-shaped stepped portion 8a of the sleeve portion 10 of the block members 8. In each of the fixing members 15, there is formed a through hole 15a extending in the X-direction for inserting the rod member 6 and a cutaway 16 at a predetermined position on the X-direction. There are also formed a screw hole 17 transversing the cutaway 16 for threadedly engaging with a fastening screw 15b and a through hole 17b for allowing the screw 15b to pass therethrough. Each block member 8 is fixed at a desired position and at a desired angle around the X-axis of the rod member 6 by fastening or loosening the fastening screw 15b of the fixing member 15.

Figure 7:
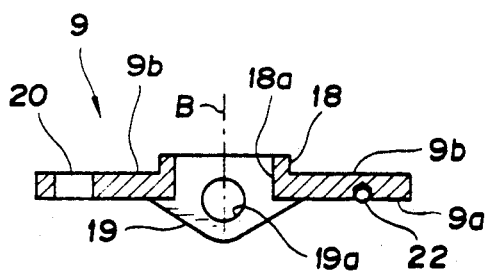
Figure 8:
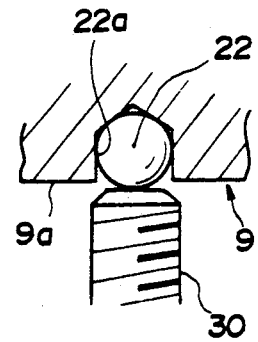
Figure 9:
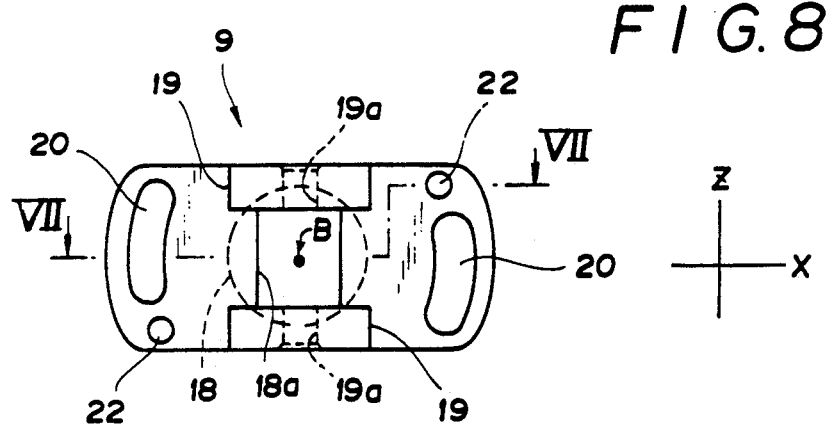

As shown in FIGS. 1 and 2, the seat member 9 is mounted on the flat surface 11 of each block member 8. As shown in FIGS. 7 to 9, the seat member 9 is a planer member having an outline like that of the flat surface 11 of the block member 8. The seat member 9 has, on its rear side, a flat surface 9b which is to be contacted with the flat surface 11 of the block member 8, and has, at its central portion, a pivot shaft 18 having an outer circular shape so as to rotatably engaged with the circular recess 12 of the block member 8. The pivot shaft 18 has a centerline B extending in a Y-direction (i.e., first direction) different than that of the X-axis. For this reason, the seat member 9 is rotatably engaged in the recess 12 of the block member 8 to be pivotably mounted on the block member 8 about the centerline B of the pivot shaft 18. Also, in the central portion in the X-axis direction of a flat surface 9a opposite the flat surface 9b, there are provided a pair of bracket portions 19 which extend forwardly to embrace the centerline B of the pivot shaft 18 in the vertical direction (in FIGS. 3 and 9). A through hole 19a is formed in each bracket portion 19 for engaging with a pivot shaft 24 to be described later. Also, a rectangular opening portion 18a is formed in a back-and-forth direction (i.e., Y-direction) between the pair of brackets 19. A bearing portion 23 of a pin holding member 7 to be described later may be received in the opening portion 18a. Furthermore, a pair of oblong holes 20 which have an arc having a center on the center axis B are formed through both sides of the pivot shaft 18 in the X-direction.

Also, as shown in FIGS. 2 and 3, within the pair of oblong holes 20, there are formed respective adjustment screws 21 used as a rotational angle adjustment mechanism about the Y-axis of the seat member 9 for fixing the seat member 9 at a desired angular position about the centerline B relative to the block member 8. An end of each adjustment screw 21 is threadedly engaged with the associated screw hole 14 of the flange portion 13 of the block member 8. Below the left oblong hole 20 and above the right oblong hole 20 shown in FIG. 9, there are provided respective recesses 22a into which balls 22 in abutment with the ends of adjustment screws 30 to be described later are embedded, as shown in FIGS. 7 to 9. Each ball 22 somewhat extends from the flat surface 9a of the seat member 9 as shown in FIG. 8 whereby the ball 22 may readily be abutted with the end portion of the adjustment screw 30.

Figure 10:
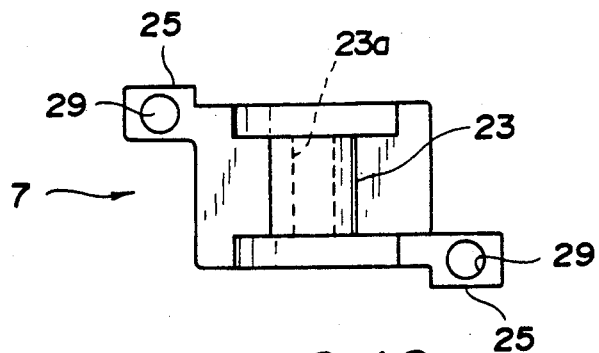
Figure 11:
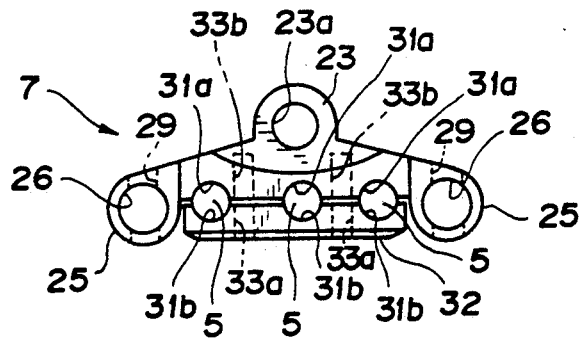
Figure 12:
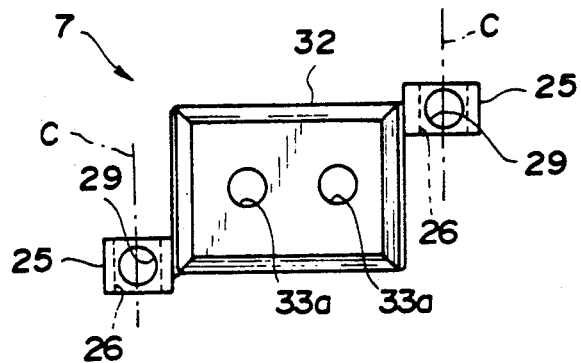

The pin holding member 7 is mounted on the front side of the seat member 9. As shown in FIGS. 10 to 12, the pin holding member 7 is provided on its rear side with a bearing portion 23 interposed between the pair of bracket portions 19 of the seat member 9 and used in combination thereof. A through hole 23a is formed in the bearing portion 23. The pivot shaft 24 is vertically inserted through the through holes 19a of the bracket portions 19 and the through hole 23a of the bearing portion 23 to thereby pivotally support the pin holding member 7 to the front side of the seat member 9 in a pivotal manner. The pivot shaft 24 is arranged to extend in a Z-direction (i.e., second direction) different than the X- and Y-directions. It is preferable that the X-, Y- and Z-directions are perpendicular to each other but it is acceptable that these directions are different from each other not to constitute a perpendicular axis system.

Figure 13:
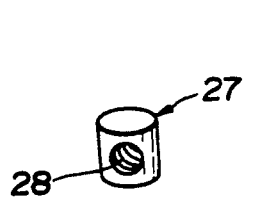
Figure 14:
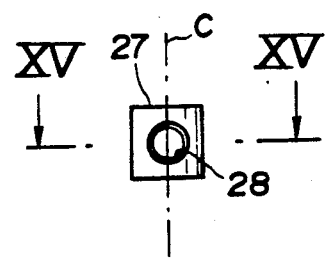
Figure 15:
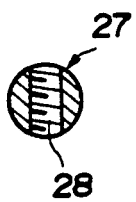

A pair of insert hole portions 25 for the adjustment screws are formed at positions, corresponding to the associated balls 22 of the seat member 9, of the pin holding member 7. The pair of insert hole portions 25 are formed in blocks and are disposed at symmetrical positions with respect to the center point of the pin holding member 7. A vertical hole 26 extending in the Z-direction is formed in the central portion of each block. As shown in FIGS. 13 to 15, a cylindrical column 27 is rotatably inserted into the vertical hole 26 of each block along its centerline C. A screw hole 28 perpendicular to the centerline C (in the direction of Y-axis) is formed in each of the cylindrical column 27. In each of the insert hole portion 25, a through hole 29 having a larger diameter than that of the screw hole 28 is formed in the Y-direction so as to correspond to the screw hole 28. An adjustment screw 30 used as an angular position adjustment mechanism for rotating the pin holding member 7 about the Z-axis is threadedly engaged with the screw hole 28 of each cylindrical column 27.

With such a structure, by rotating each screw 30, the slant angle of the pin holding member 7 is changed, and at this time, the cylindrical column 27 is rotatable along the centerline C within the insert hole portion 25. Accordingly, the end of the adjustment screw 30 is always capable of contacting with the ball 22 of the seat member 9 regardless the extent of the slant angle of the pin holding member 7. Thus, the rotational operation of the adjustment screw 30 is carried out smoothly, and the posture changing operation of the pin holding member 7 may readily be attained.

As described above, upon the positional adjustment of the pins 5 attached to the pin holding members 7, it is sufficient to only rotate the respective adjustment screw 30 on both sides of the pivot shaft 24 along the Z-direction for performing the adjustment in Z-direction. In contrast, according to the prior art, it is necessary to separately perform the screw operations such as loosening the fastening screws, thereafter rotating the pin holding members and again fastening the fastening screws with the holding members being located at a desired position, and the operations for pin holding members. However, accordingly to the present invention, such troublesome operations may be avoided.

On the front side of the pin holding member 7, in the Z-direction, these are formed a plurality (three in the embodiment) of long grooves 31a for receiving the pins 5. A rectangular pin retaining plate 32 having a plurality of long grooves 31b at positions corresponding to the long grooves 31a for receiving the pins 5 is provided on the front side of the pin holding member 7. A pair of through holes 33a are formed in the pin retaining plate 32. A pair of screw holes 33b are formed at positions corresponding to the through holes 33a in the pin holding member 7. Accordingly, as shown in FIGS. 2 and 3, a pair of fastening screws 33 are inserted into the through holes 33a of the pin retaining plate 32 and are threadedly engaged with the screw holes 33b, whereby the pins 5 may be detachably held in the long grooves 31a and 31b.

The operation of the bone fixing device according to the invention will now be described. First of all, the rod member 6 is arranged along the longitudinal direction of the bone 4. The pins 5 are inserted into the broken bone segments 4a and 4b to be fixed to each other. At the same time, the pins 5 are mounted on the pin holding members 7 by fastening the fastening screws 33 relative to the holding members 7. At this time, each adjustment screw 21, 30 and fastening screw 15b are loosened. Since the pair of pin holding members 7 are mounted on the rod member 6 through the pair of block members 8 and the seat members 9, each bone segment 4a, 4b is arranged substantially in the same direction as the longitudinal direction of the rod member 6.

Subsequently, under the condition that the fastening screws 15b are loosened, the block members 8 are moved at desired positions in the axial direction along the rod member 6 and are rotated through a desired angle. Thereafter, the fastening screws 15b of the fastening members 15 are rotated and fastened to thereby fix the respective block members 8 to the rod member 6. Also, after the pivot shafts 18 of the seat members 9 have been rotated through a desired angle about the centerline B, the respective adjustment screws 21 are fastened, to thereby fix the respective seat members 9 to the associated block members 8 to determine the angular position about the Y-axis.

Furthermore, the angular position adjustment of each pin holding member 7 along the pivot shaft 24 in the Z-direction is performed by using the respective adjustment screws 30 of the pin holding members 7. Namely, the angle of each pin holding member 7 relative to the seat member 9 is changed while rotating each adjustment screws 30 on each side of the pivot shaft 24.

With such operations, the pins 5 are finely positionally adjusted so that the positional relationship between the broken bone segments 4a and 4b is suitably determined with ease. The respective bone segments 4a and 4b may be exactly held and bonded to each other.

As has been described above, according to the present invention, since the substantially rectangular seat members 9 are supported to the block members 8 through the flat surfaces 9b and the pin holding members 7 are swingably held relative to the seat members 9, it is unnecessary to provide any through holes in the block members 8 and it is sufficient to use a single rod member 6 in the X-direction. Also, it is possible to suppress the extrusion of the device in the Y-direction. It is therefore possible to simplify the structure of the device as a whole and to reduce a weight of the device, which leads to a convenient treatment of the device.

A second embodiment of the present invention will now be described with reference to FIGS. 18 through 25.

In FIGS. 18 through 23, reference numeral 114 designates a bone composed of two broken bone segments 114a and 114b. A bone fixing device 101 to which the invention pertains is mounted on the broken bone segments 114a and 114b. The attachment of the fixing device 101 is performed by fixedly inserting the attachment pins 115 into the respective broken bone segments 114a and 114b.

The bone fixing device 101 is provided with a single rod member 116 to be arranged along the longitudinal direction of the bone segments 114a and 114b. Two pairs of pin holding members 117a and 117b are mounted on the rod member 116. The pin holding members 117a and 117b are mounted on the rod members 116 through first and second block members 118a and 118b and seat members 119a and 119b, respectively.

The first block member 118a is provided with a sleeve portion 120a through which the rod member 116 is to be inserted. The second block member 118b is provided with a sleeve portion 120b for holding a bearing 151 within its interior and allowing the rod member 116 to be slidable in the interior. A single flat surface 121 is formed at the portion along the centerline of the sleeve portion 120a, 120b. A circular recess 122 for bearing is formed in the central portion of the flat surface 121. Also, a pair of flange portions 123 are flush with and formed on both sides of the sleeve portion 120a, 120b. Screw holes 123a are formed in the flange portions 123. As shown in FIG. 20, a fastening member 124 for fixing the block member 118a to a desired position of the rod member 116 is provided on the left side of an L-shaped stepped portion 124b of the sleeve portion 120a of the first block member 118a. The fastening member 124 has substantially the same structure as that shown in FIGS. 16 and 17. A cutaway portion 124c is formed at a position along the X-axis in the fastening member 124 and is provided with a fastening screw 125. Therefore, by fastening or loosening the fastening screw 125, the block member 118a may be located at a desired position in the X-direction and at a desired angular position about the X-axis relative to the rod member 116.

The seat members 119a and 119b are mounted on the flat surfaces 121 of the block members 118a and 118b. The seat members 119a and 119b are planar members having an outline which is partially the same as that of the flat surfaces 121 of the block members 118a and 118b. A pivot shaft 126 having an outer circular shape to be engaged with the circular recess 122 of the block member 118a, 118b is formed in the central portion of the rear side of the block member. The pivot shaft 126 has a centerline extending in the Y-direction perpendicular to the X-direction. For this reason, the seat members 119a and 119b are rotatably engaged with the recesses 122 of the block members 118a and 118b and are rotatable about the centerlines of the pivot shafts 126, respectively. A pair of up-and-down bracket portions 127 embracing the pivot shaft 126 projecting forwardly are provided on the central portion of the front side of each of the seat members 119a and 119b. A through hole 127a for engaging a pivot shaft 131 to be described later is formed in each bracket 127. Also, in the same manner as in the arrangement shown in FIG. 9, a rectangular opening portion 126a is formed back and forth (in the Y-direction) between the brackets 127. A bearing portion 130 of each of the pin holding members 117a and 117b to be described later may be received in the opening portion 126a. Furthermore, a pair of long holes 128 having an arcuate shape are penetratingly provided on both sides in the X-direction while embracing the pivot shaft 126 in each of the seat members 119a and 119b.

Also, as shown in FIG. 19, adjustment screws 129 are inserted into the pair of long holes 128 as an angular motion adjustment mechanism around the Y-axis of the seat members 119a and 119b for fixing the seat members 119a and 119b at desired angular positions relative to the block members 118a and 118b. The ends of the adjustment screws 129 are threadedly engaged with the screw holes 123a of the flange portions 123 of the block members 118a and 118b. Also, below the left long hole 128 and above the right long hole 128, there are formed recesses within which balls 139 to be brought into contact with the ends of adjustment screws 134 to be described later are embedded. The respective balls 139 project somewhat from the surfaces of the seat members 119a and 119b to thereby facilitate the direct contact between the balls 139 and the adjustment screws 134.

The pin holding members 117a and 117b are provided on the front surfaces of the seat members 119a and 119b. The pin holding members 117a and 117b are pivotally supported to front sides of the seat members 119a and 119b by providing bearing portions 130 used in combination with the brackets 127 of the seat members 119a and 119b and inserting pivot shafts 131 between the brackets 127 and the bearing portions 130. Each pivot shaft 131 is arranged to extend in the Z-direction perpendicular to the X- and Y-directions.

A pair of adjustment screw insert portions 132 are projectedly formed at positions, corresponding to the balls 139 of the seat members 119a and 119b, of the pin holding members 117a and 117b. The pair of adjustment screw insert portions 132 are in the form of blocks. A vertical hole 132a is formed in the central portion of the block along the Z-direction. A cylindrical column 133 is rotatably inserted around the Z-axis direction into the vertical hole 132a. A screw hole is formed in a direction (Y-axis) perpendicular to the centerline of the cylindrical column 133 (Z-axis) in the cylindrical column 133. A through hole is formed in each adjustment screw insert portion 132 at a position where the screw hole is aligned with the through hole (see FIGS. 13 to 15). Accordingly, the end of the adjustment screw 134 to be inserted into the through hole of the adjustment screw insert portion 132 and the screw hole of the cylindrical column 133 may be contacted with the ball 139 on the seat member 119a, 119b irrespective of the extent of the slant of the pin holding member 117.

Long grooves 135a for receiving the pins 115 are formed on the front side portion of the pin holding member 117. A rectangular pin retainer portion 136 having long grooves 135a corresponding to the long grooves 135a covers the front portion of the pin holding member 117. Therefore, the pins 115 are detachably held in the pin holding member 117 by fastening screws 137.

On the opposite side of the installation of the pin holding members 117a and 117b with respect to the rod member 116, there is provided an actuator 138 for slidingly moving the right pin holding member 117a relative to the rod member 116.

Figure 22:
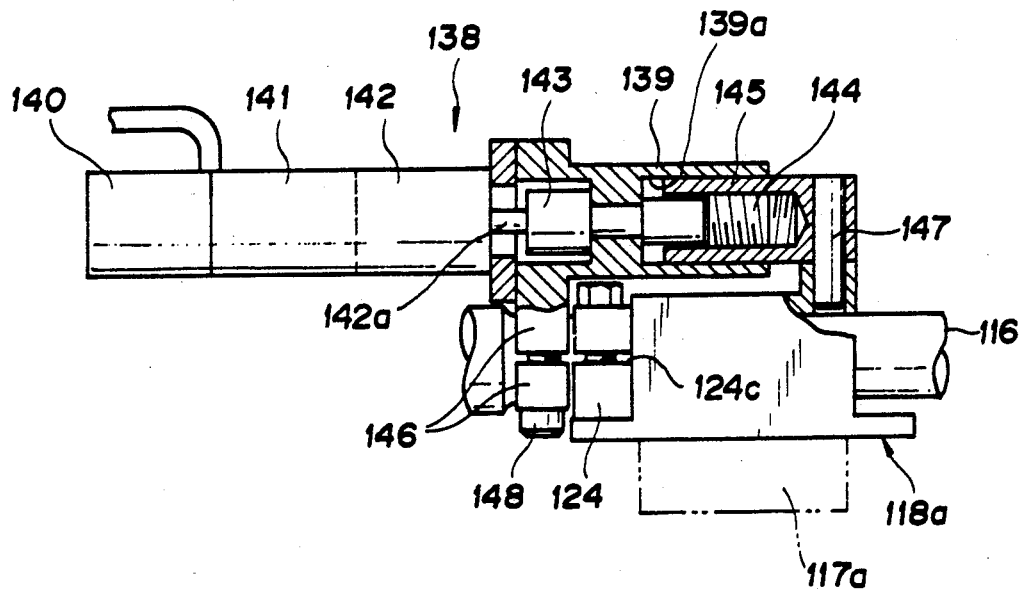
Figure 23:
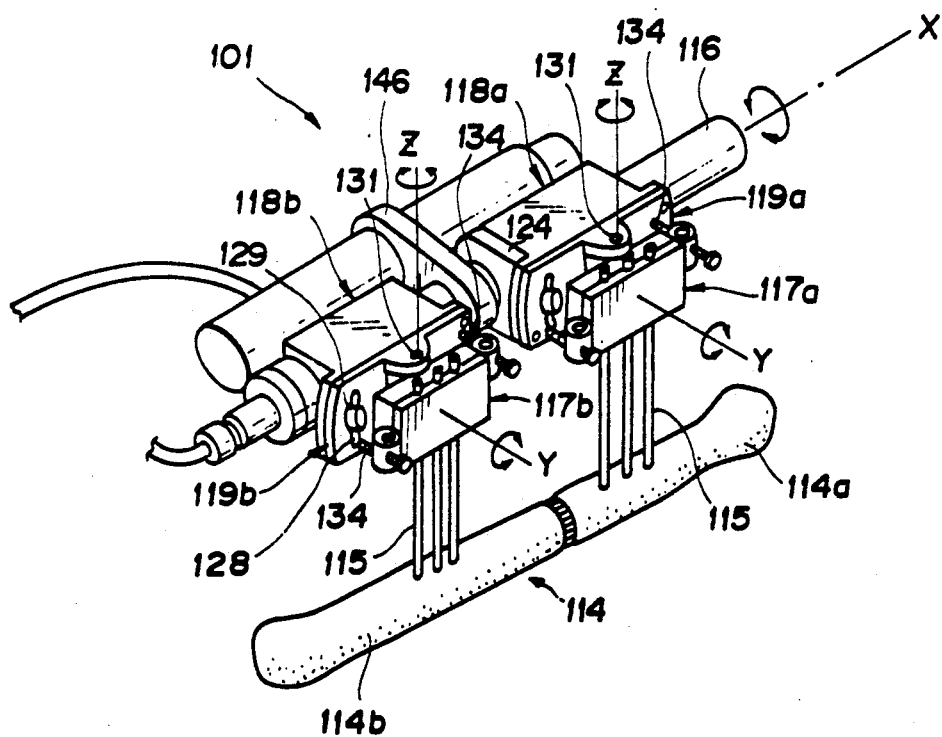

In the actuator 138, an encoder 140 for sending and receiving signals with respect to a control unit 163, a motor 141 driven in accordance with command signals from the encoder 140 and a reduction gear mechanism 142 drivingly connected to the motor 141 are fixed in a row within a sleeve-like casing 139 (FIG. 22). Further, a rotational screw 144 is connected to an output shaft 142a of the reduction gear mechanism 142 by a coupling 143. A screw sleeve 145 threadedly engaged with the rotational screw 144 and slidingly moving within a cylinder 139a of the casing 139 is extendable or retractable within the casing 139. The cylinder 139a and the rotational screw 144 have a common centerline in parallel to the rod member 116.

The casing 139 of the actuator 139 is held to the rod member 116 by the fastening member 146. The screw sleeve 145 which reciprocatingly moves and which is provided with a screw 145a is connected to the block member 118a of the right pin holding member 117a by a connection pin 147. Reference numeral 148 denotes a fastening screw for fastening or loosening, relative to the rod member 116, the fastening member 146 mounted integrally with the casing 139 (FIGS. 19 and 20).

As shown in FIG. 19, a spline shaft 149 is coaxially projected to the left and fixed to the left end portion of the rod member 116. A rod-like contact 150 is fixed to an axial center of the spline shaft 149. On the outside of the spline shaft 149, the block member 118b holding the left pin holding member 117b is mounted through a bearing 151. Since the bearing 151 is fixed to the sleeve portion 120b of the block member 118b, the spline shaft 149 is relatively retractable or extendable only in the X-direction within the block member 118b through the bearing 151. As a result, the left pin holding member 117b mounted on the block member 118 is only moved in the X-direction relative to the rod member 116 but not rotatable.

A load cell 152 which is confronted with the tip end of the contact 150 positioned at the end of the rod member 116 and which is used as a detector is mounted through a load cell holder 153 on the left end of the block member 118b of the left pin holding member 117b.

The load cell holder 153 is provided a sleeve 154 for clamping the load cell 152 in its interior. A male screw 155 formed around the sleeve 154 is engaged with a left end female screw 156 of the block member 118b, whereby the load cell 152 is retained by the block member 118b.

Figure 24:
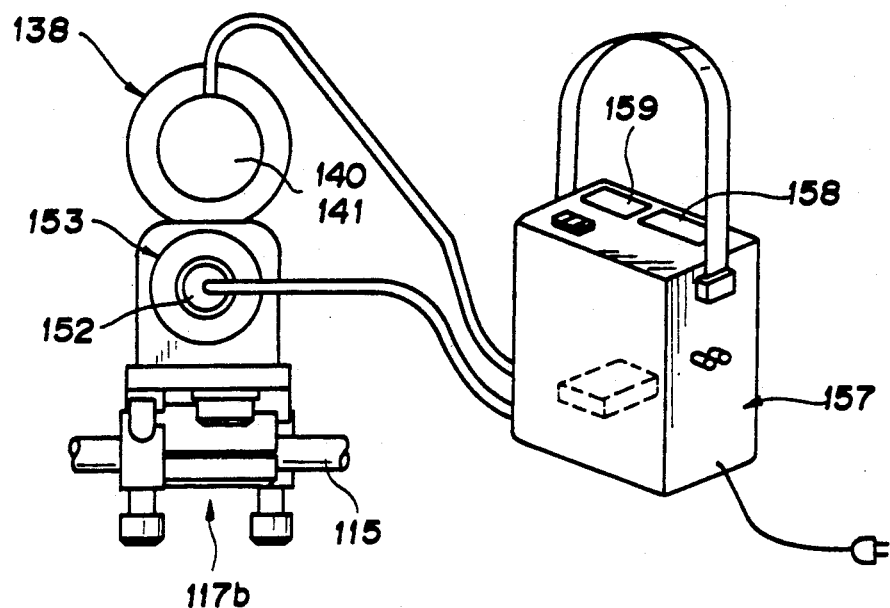

As shown in FIG. 24, the control unit 157 is provided for supplying an electric power to the motor 141 of the actuator 138, outputting signals to the encoder 140, processing the output signals from the encoder 140 to indicate a predetermined pattern and processing the signals from the load cell 152.

Subsequently, the operation of the bone fixing device 101 will now be described. First of all, the rod member 116 is arranged in the longitudinal direction of the bone 114. The pins 115 are inserted into the broken bone segments 114a and 114b and fixed to each other. The pins 115 are mounted on the pair of pin holding members 117a and 117b by using the fastening screws 137. At this time, the respective adjustment screws 129, 134 and the fastening screws 125 and 148 are loosened. Thus, the rod member 116 is arranged in the longitudinal direction of the bone 114.

Subsequently, under the condition that the fastening screws 125 are loosened, the block member 118a is moved up to a desired position along the axial direction of the rod member 116. At the same time, the block member 118a is rotated through a desired angle. Thereafter, the fastening screws 125 are fastened to thereby the block member 118a to the rod member 116. Also, after the seat members 119a and 119b have been rotated through a desired angle around the pivot shafts 126 in the Y-direction, the respective adjustment screws 129 are fastened to thereby fix the seat members 119a and 119b to the block members 118a and 118b.

Further, by using the adjustment screws 134 of the pin holding members 117a and 117b, the rotational angle adjustment around the pivot shaft 131 in the Z-direction of the pin holding members 117a and 117b is carried out. Namely, the angle of the pin holding members 117a and 117b to the seat members 119a and 119b is changed while rotating the respective adjustment screws 134 on both sides of the pivot shaft 131.

With such operations, the pins 115 are finely positionally adjusted, and the positional relationship between the broken bone segments 114a and 114b is suitably determined, so that the bone segments 114a and 114b are exactly held and bonded to each other.

Subsequently, an explanation will be made as to the case where an elongation or contraction is applied to a damaged part of the bone 114 held by the bone fixing device 101 according to the invention for the purpose of reducing the medical treatment duration.

Figure 25:
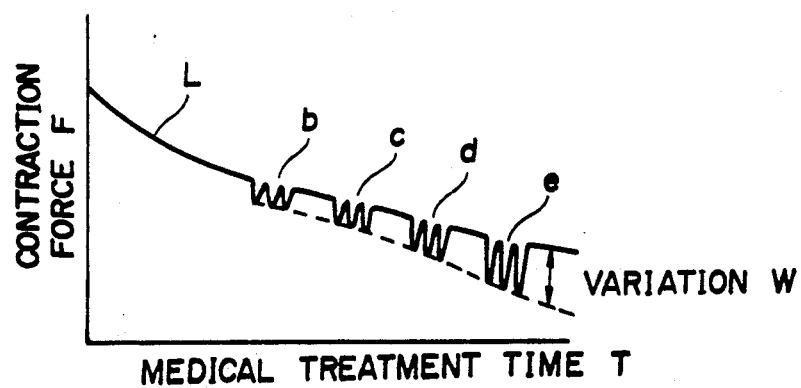

In a medical treatment process of leg elongation for a patient suffering from dwarf illness or leg break, a shift stimulus of the elongation and contraction is applied to the damaged part of the bone as shown in FIG. 25. Namely, the contraction force F relative to the medical treatment time T is represented by a curve L. As the medical treatment time T lapses, the damaged part become hard. Therefore, the contraction force F from the bone 114 is gradually reduced. If the shift stimulus is applied to the damaged part by changing the stroke of the screw sleeve 145 at the times b, c, d and e during the medical treatment time T, the bone 114 becomes hard as the medical treatment time lapses. As a result, the repulsive force received from the bone 114 will be increased to increase the variation W gradually. Thus, in order to elongate or retract the bone 114, the actuator 138 is mounted on the rod member 116 by the fastening member 146. At the same time, the screw sleeve 145 and the right block member 118a are connected to each other by the connection pin 147. Then, the fastening screws 125 are loosened so that the right block member 118a is slidable relative to the rod member 116. On the other hand, the fastening screws 148 of the fastening member 146 of the actuator 138 are fastened, so that the casing 139 of the actuator 138 is fixed to the rod member 116. Subsequently, the stroke of the screw sleeve 145 is set by the set portion 158 of the control unit 157. At the same time, a timing is set so that the shift stimulus may be applied to the bonded bone 114 at a constant interval. The mode for applying the shift stimulus in the medical treatment for the broken bone or the elongation speed for the dwarf illness varies in accordance with a personal patient. While reading the shift stimulus amount (elongation or contraction amount), the number of times of stimulation, the cycle, the shift pattern, the reduction force F applied from the bone 114, the repulsive force of the bone, the stroke of the screw sleeve 145, and the elongation or contraction of the bone 114 on the indicator 159 in accordance with the output signals from the load cell 152, the optimum medical treatment is carried out for every patient in view of the various factors.

When the signal is supplied from the control unit 157 to the encoder 140, the motor 141 is rotated by a predetermined number of revolution according to the command signal from the encoder 140. As a result, the rotational screw 144 is rotated through the reduction gear mechanism 142 relative to the screw sleeve 145 of the actuator 138 by a predetermined number of turns. The rotational screw 144 is fixed to the rod member 116, whereas the screw sleeve 145 is connected to the bone 114 through the block member 118a that is slidable relative to the rod member 116. Accordingly, the elongation or contraction is imparted to the bone 114, and the repulsive force from the bone 114 corresponding to the elongation or contraction is transmitted to the rod member 116 through the actuator 138. The left end of the contact 150 projecting leftwardly from the left end of the rod member 116 depresses the load cell 152 fixed to the left side pin holding member 117b. The load cell 152 detects the depression force to thereby output an associated signal to the control unit 157. Accordingly, the variation W of the contraction force applied to the bone 114 is displayed on the indicator 159 of the control unit 157 through the load cell 152.

Thus, since the load cell 152 is disposed on the axis of the rod member 116, it is possible to enhance an accuracy of the detection value. Also, since the rod member 116 is not of the double structure type but of the single type having no extension or retraction, the detection value is more accurate.

Incidentally, upon using the bone fixing device 101, it is possible to perform a sterilization treatment of the fixing device with steam or the like by removing the load cell holding member 153 away from the block member 118b.

Figure 26:
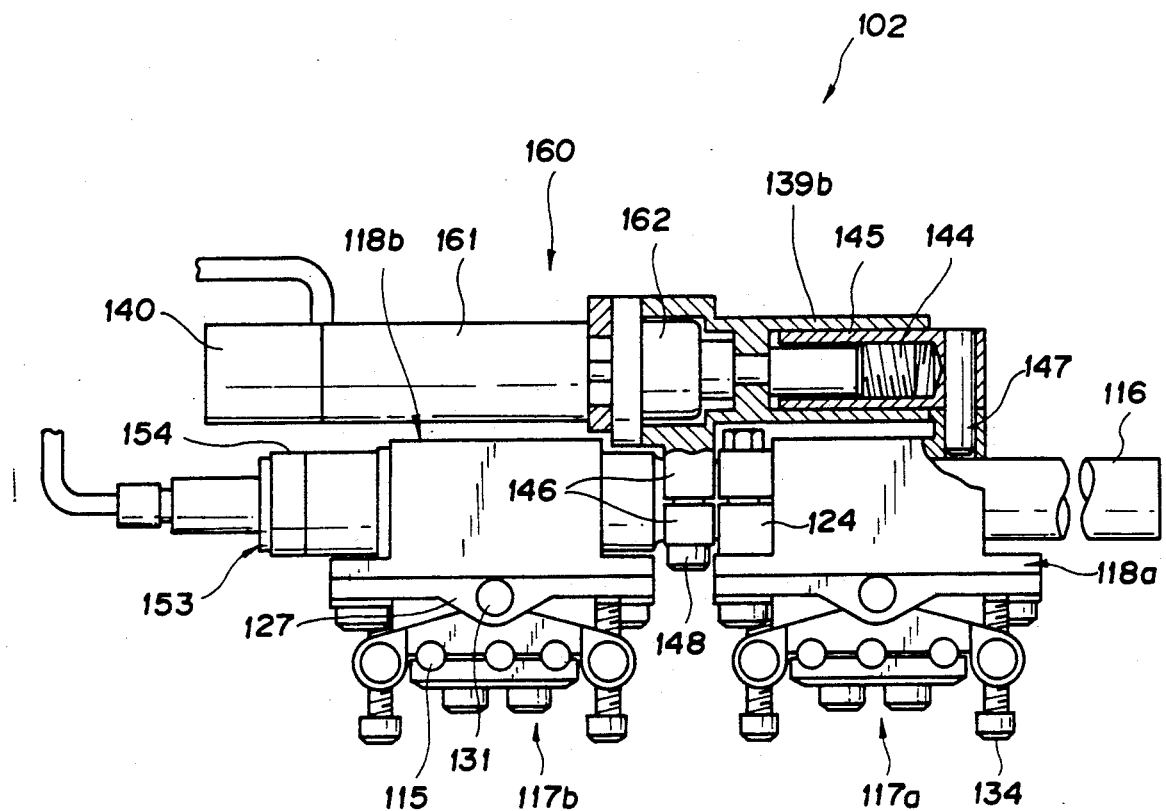
FIG. 26 is a partially fragmentary view, from which the reciprocating portion of the actuator has been removed, showing the third embodiment of the invention.

FIG. 26 is a view showing a bone fixing device 102 according to a third embodiment of the invention. In the case where the bone is not to be elongated and contracted but to be simply elongated, it is necessary to use an actuator that may reduce a moving speed of the screw sleeve 145 instead of the foregoing actuator 138. The moving speed is, for example, 1 mm/day.

As shown in FIG. 26, in order to ensure such a moving speed of the screw sleeve 145, the actuator 160 in accordance with the third embodiment includes a motor 161 with a reduction gear mechanism, controlled by the encoder 140, a rotational screw 144 threadedly engaged with the screw sleeve 145, and another reduction gear mechanism 162 connected between the motor 161 and the rotational screw 144. Reference character 139b denotes a casing. With such an arrangement, the rotational speed of the motor 161 with the reduction gear mechanism is further reduced and is transmitted to the rotational screw 144, thereby reducing the moving speed of the screw sleeve 145.

In order to interchange the actuators 138 and 160 with each other, the fastening screw 148 of the fastening member 146 is removed to thereby dismount the fastening member 146, which may readily be attained.

Figure 27:
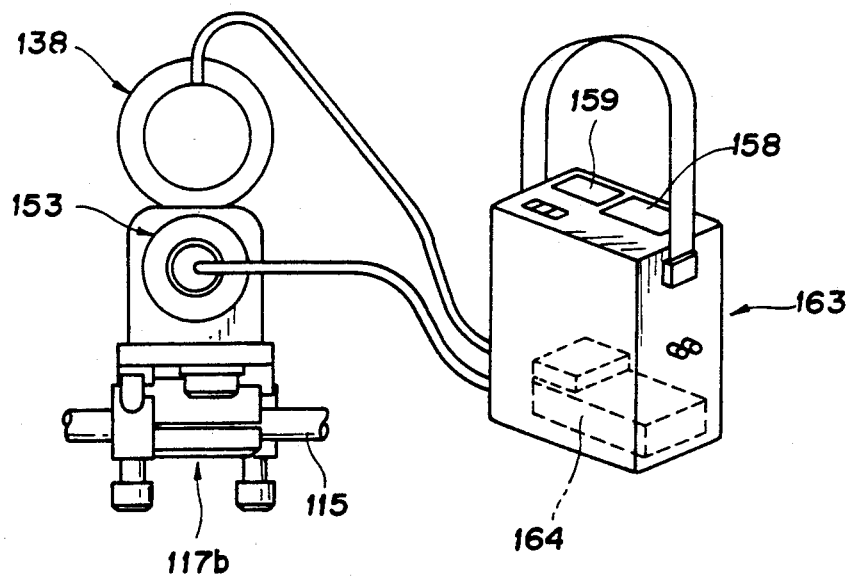
FIG. 27 is an illustration showing the fixing device including the control unit.

In the first to third embodiments, as shown in FIG. 27, if a chargeable battery 164 is incorporated and used as an electric source of the control unit 163, the system is portable, and it is possible to use the fixing device 101, 102 at any desired location.

According to the invention, as described above, since the load cell 152 is located on the axis of the rod member 116, it is possible to enhance the precision in detection value. Also, since the rod member 116 is not of the double structure type but of the simple type without any retraction/extension to thereby further enhance the accuracy of the detection value. Accordingly, it is advantageous to detect the variation of the reduction force applied to the damaged part of the bone 114 and suitably effect the medical treatment in comparison with the conventional treatment.

What is claimed is:

1. A bone fixing device comprising:
   (a) a single rod member adapted to be disposed in a longitudinal direction of a bone;
   (b) at least two block members mounted on said rod member and fixable to any position in an axial direction and any angular position around the axial direction; and
   (c) pin holding means mounted on the respective block members for holding and positionally adjusting pins to be fixed to the bone around a first direction and a second direction which are different from the axial direction, each of said pin holding means including;
   a seat member mounted on each block member in said first direction and adjustable around a pivot axis directed in said first direction by the block member, and
   a pin holding member for detachably holding the pins to be inserted into the bone, said pin holding member being mounted on the seat member in the first direction and being swingably adjustable around a pivot axis directed in the second direction.

2. The bone fixing device according to claim 1, wherein said axial direction, said first direction and said second direction are substantially perpendicular to each other.

3. The bone fixing device according to claim 1, wherein each of said block members includes a sleeve portion having a hole through which said rod member passes, a flat surface being parallel to an axial line of said sleeve portion, and a circular recess formed in a central portion of the flat surface and an axial centerline in the first direction;
   each of said seat members includes a flat surface to come into surface contact with the flat surface of the block member, a pivot shaft formed in a central portion of the flat surface, rotatably engaged with said circular recess of said block member and having a circular outline, and a pair of brackets disposed on a surface opposite to said flat surface to project in the second direction while embracing an axial centerline of said pivot shaft; and
   each of said pin holding members includes a bearing portion interposed between said pair of brackets and swingably pivoted to said brackets by a pivot shaft directed in the second direction, and a pin retainer portion for clamping said pins.

4. The bone fixing device according to claim 3, further comprising a means for adjusting an angular movement of each of said seat members, wherein a pair of screw holes are formed outwardly on both sides of the circular recess in the block member, a pair of arcuate oblong holes are formed at positions, corresponding to the screw holes, of the seat member, and a pair of adjustment screws pass through the oblong holes and threadedly engage with the screw holes to fasten the seat member to the block member.

5. The bone fixing device according to claim 3, further comprising a means for rotatably adjusting the pin holding member, wherein a pair of adjustment screws engage with the pin holding member to embrace the pivot shaft on both sides, and an end portion of each of the adjustment screws is brought into contact with the seat member.

6. The bone fixing device according to claim 5, wherein a pair of ball members which come into contact with the end portions of the adjustment screws, respectively, are embedded in the flat surface of the seat member, and the ball members somewhat project from the flat surface.

7. The bone fixing device according to claim 5, wherein a pair of adjustment screw insert portions each having a through hole which passes through the associated adjustment screw are formed in a symmetric relation with respect to a central point of said pin holding member, a circular column having an axial centeraxis in the second direction is rotatably engaged in each of said adjustment screw insert portions, and a screw hole with which the adjustment screw threadedly engages is threadedly formed in the first direction.

8. The bone fixing device according to claim 1, further comprising a means for fastening each of the block member to the rod member, wherein a fastening member is fixed to a sleeve portion having a hole through which the rod member passes, a hole through which the rod member passes is formed in the axial direction in the fastening member, a cutaway portion is formed in a position along in the axial direction in the fastening member, and a fastening screw is threadedly engaged through said cutaway portion.

9. A bone fixing device comprising:
a single rod member adapted to be disposed in a longitudinal direction of a bone;
at least two block members mounted on said rod member and fixable to any position in an axial direction and any angular position around the axial direction;
pin holding means mounted on the respective block members for holding and positionally adjusting pins to be fixed to the bone around a first direction and a second direction which are different from the axial direction;
an actuator fixed to the rod member for moving in the axial direction one of the block members slidable relative to said rod member, thereby imparting elongation/contraction force to the bone;
a detector fixed to the other of said block members and coming into contact wich a contact located at an end portion of said rod member for detecting a repulsive force from the bone; and a control unit for receiving detection signals from the detector and for outputting command signals to said actuator.

10. The bone fixing device according to claim 9, wherein said actuator includes:
a casing having a cylinder formed in parallel to the axial centerline of said rod member and positionally adjustably fixed to said rod member by a fastening member;
a screw sleeve swingable in said cylinder, connected to one block member and having a screw in its inner surface; and
a rotational screw drivingly rotated by a drive source mounted on said casing and threadedly engaged with the screw of the screw sleeve to extend/retract said screw sleeve within said cylinder.

11. The bone fixing device according to claim 10, wherein said drive source includes an encoder for receiving and sending signals with respect to said control unit, a motor drivingly controlled by a command signals from said encoder, and a speed reduction means connected to said motor to thereby rotate the rotational screw.

12. The bone fixing device according to claim 11, wherein said motor comprises a motor with a speed reduction means.

13. The bone fixing device according to claim 9, wherein said control unit comprises a chargeable battery.

14. The bone fixing device according to claim 9, wherein said detector is mounted through a retainer member on said other block member, a spline shaft having an axis to which the rod-like contact is fixed is coaxially fixed to an end portion of the rod member, and said spline shaft is extendable/retractable in the axial direction through a bearing within the block member.

* * * * *